United States Patent [19]

Kao et al.

[11] Patent Number: 5,723,673
[45] Date of Patent: Mar. 3, 1998

[54] PROCESS FOR PREPARING AMIDES OF N-ALKYL POLYHYDROXYALKYLS

[75] Inventors: Junan Kao, Kobe, Japan; Ephraim Lamar Kelly, Batavia, Ohio; Vicki Lynn Weber, Cincinnati, Ohio; Michael Steven Gibson, Loveland, Ohio; Donald Benjamin Appleby; Joseph Fredrich Sherman, both of Cincinnati, Ohio; Ronald Edward Pegoli; Mary Celine Schneider, both of Batavia, Ohio; Terry Franklin Formyduval; Larry Nelson Hawkins, both of Cincinnati, Ohio

[73] Assignee: The Procter & Gamble Company, Cincinnati, Ohio

[21] Appl. No.: 474,857

[22] Filed: Jun. 7, 1995

[51] Int. Cl.$^6$ .................................. C07H 209/44
[52] U.S. Cl. .......................... 564/487; 564/469; 252/548; 554/66; 554/68; 554/69; 554/70; 554/187; 554/188
[58] Field of Search .................. 554/70, 187, 188, 554/66, 68, 69; 564/469, 487; 252/548

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,653,932 | 9/1953 | Schwartz | 260/211 |
| 2,662,073 | 12/1953 | Mehltretter et al. | 260/102 |
| 2,703,798 | 3/1955 | Schwartz | 260/211 |
| 2,844,609 | 7/1958 | Tesoro | 260/404 |
| 2,891,052 | 6/1959 | Boettner et al. | 260/211 |
| 2,954,347 | 9/1960 | St. John et al. | 252/109 |
| 2,991,296 | 7/1961 | Scherr | 260/404 |
| 2,993,887 | 7/1961 | Zech | 260/211 |
| 3,257,436 | 6/1966 | Lindner | 260/404 |
| 3,285,856 | 11/1966 | Lew | 252/152 |
| 3,576,749 | 4/1971 | Megson et al. | 252/132 |
| 3,637,495 | 1/1972 | Eckert et al. | 252/8.8 |
| 3,704,228 | 11/1972 | Eckert | 252/117 |
| 3,920,586 | 11/1975 | Bonaparte et al. | 252/531 |
| 3,929,678 | 12/1975 | Laughlin et al. | 252/526 |
| 3,985,669 | 10/1976 | Krummel et al. | 252/116 |
| 3,988,255 | 10/1976 | Seiden | 252/107 |
| 4,094,808 | 6/1978 | Stewart et al. | 252/186 |
| 4,129,511 | 12/1978 | Ogoshi et al. | 252/140 |
| 4,223,163 | 9/1980 | Guilloty | 568/618 |
| 4,292,212 | 9/1981 | Melby | 252/547 |
| 4,483,781 | 11/1984 | Hartman | 252/174.12 |
| 4,540,821 | 9/1985 | Larkin et al. | 564/473 |
| 4,565,647 | 1/1986 | Llenado | 252/354 |
| 4,664,839 | 5/1987 | Rieck | 252/175 |
| 4,704,224 | 11/1987 | Saud | 252/132 |
| 4,843,154 | 6/1989 | Klein et al. | 536/4.1 |
| 5,009,814 | 4/1991 | Kelkenberg et al. | 252/528 |
| 5,334,764 | 8/1994 | Scheibel et al. | 564/487 |
| 5,338,487 | 8/1994 | Connor et al. | 252/357 |
| 5,449,770 | 9/1995 | Kao et al. | 564/487 |
| 5,571,934 | 11/1996 | Papenfuhs et al. | 554/70 |
| 5,625,098 | 4/1997 | Kao et al. | 564/487 |

FOREIGN PATENT DOCUMENTS

| | | | |
|---|---|---|---|
| 206283 | 6/1956 | Australia. | |
| 0220676 A1 | 5/1987 | European Pat. Off. | C07C 103/38 |
| 0255033 A2 | 2/1988 | European Pat. Off. | C07H 1/04 |
| 0282816 A2 | 9/1988 | European Pat. Off. | A61K 7/48 |
| 0285768 A1 | 10/1988 | European Pat. Off. | C11D 3/32 |
| 0422508 A2 | 4/1991 | European Pat. Off. | A61K 7/06 |
| 1580491 | 9/1969 | France. | |
| 2657611 | 8/1991 | France | C07H 5/06 |
| 53839 | 2/1967 | German Dem. Rep. . | |
| 13746 | 9/1957 | Germany. | |
| 23346 | 6/1962 | Germany. | |
| 2038103 | 2/1972 | Germany | C11D 7/42 |
| 2226872 | 12/1973 | Germany. | |
| 2404070 | 8/1975 | Germany. | |
| 420518 | 11/1934 | United Kingdom. | |
| 519381 | 3/1940 | United Kingdom. | |
| 771423 | 4/1957 | United Kingdom. | |
| 809060 | 2/1959 | United Kingdom. | |
| 2242686 | 10/1991 | United Kingdom | C11D 1/722 |

OTHER PUBLICATIONS

The Reaction of Glucose with Some Amines, Mitts and Hixon, JACS, vol. 66, (1944), pp. 483–486.

[23] 1–Amino–1–deoxy–D–glucitol, Long and Bollenback, Meth. Carbohyd. Chem., vol. 2, (1963), pp. 79–83.

Synthesis of $^{14}$C–Labeled N–Methylglucamine, Heeg et al., Can. J. of Pharmaceutical Sciences, vol. 10, No. 3, (1975), pp. 75–76.
Relative Stabilities of d–Glucose–Amine Derivatives, Mohammad and Olcott, JACS, Apr. 1947, p. 969.
Detergents Based on Sugars, Kelkenberg, tenside Surfactants Detergents, vol. 25, #1 (1988).
Synthesis of Long Chain N–Alkyllactylamines from Unprotected Lactose—A New Series of Non–Ionic Surfactants, Latge et al., J. Dispersion Science and Technology, 12(3&4), pp. 227–237 (1991).
"N–D–Gluco–N–methylalkanamide Compounds, a New Class of Non–Ionic Detergents for Membrane Biochemistry", Biochem. J. (1982), vol. 207, pp. 363–366, Hildreth carbohydrate amphiphiles, Liquid Crystals, 1988, vol. 3, No. 11, pp. 1569–1581, J. W. Goodby et al.

*Primary Examiner*—James O. Wilson
*Attorney, Agent, or Firm*—Robert B. Aylor

[57] ABSTRACT

N-alkyl polyhydroxy alkyl amines such as N-methyl glucamine having a Gardner Color of less than 1 are reacted with sources of fatty acyl groups such as methyl esters, anhydrides, and/or fatty acids that have greater than 98% transmittance at 460 nm in organic hydroxy solvents such as methanol to prepare N-alkyl polyhydroxy amine amides with good color. The N-alkyl polyhydroxyamines can be purified by crystallization, and/or subjected to reductive bleaching, to provide superior color. The reaction is preferably carried out at low temperature for short periods of time and with low catalyst levels to minimize formation of cyclic products. The resulting amide product can be further purified by treatment with anionic and cationic exchange resins to remove soap and amine impurities. The anionic ion exchange resin can be readily regenerated by acidifying it followed by washing with an organic solvent.

19 Claims, No Drawings

PROCESS FOR PREPARING AMIDES OF N-ALKYL POLYHYDROXYALKYLS

FIELD OF THE INVENTION

The present invention relates to an improved process for preparing amides of N-alkyl polyhydroxyalkyl amines, especially ones having good color and low levels of undesirable by-products.

BACKGROUND OF THE INVENTION

The manufacture of N-alkyl polyhydroxyalkyl amines (N-alkyl polyhydroxy amines), such as N-methylglucamine, and the fatty acid amides thereof, has been known for many years, and such materials are available commercially. Recently, there has been occasion to employ N-alkyl polyhydroxy amines, e.g., in reactions with, e.g., fatty acid esters to prepare fatty acid polyhydroxy amide detersive surfactants for use in cleaning products. It has been determined that care must be taken in preparing N-alkyl polyhydroxy amines and amides to provide the amides with the best color.

The present invention affords access to high quality polyhydroxy fatty acid amide surfactants. The present invention provides means for preparing N-alkyl polyhydroxy amine amides which are almost water white, especially amides of N-methylglucamine, in high yields, and more especially, amides of N-methylglucamine containing low levels of cyclic materials as hereinafter disclosed.

BACKGROUND ART

Glucose reductive amination processes are disclosed in U.S. Pat. No. 2,016,962, Flint et al., issued Oct. 8, 1935.

U.S. Pat. No. 1,985,424, Piggott, issued Dec. 25, 1934, discloses manufacturing "textile assistants" by reacting (a) the product of heating glucose and aqueous methylamine in presence of hydrogen and a hydrogenating catalyst under pressure with (b) an organic carboxylic acid such as stearic acid or oleic acid. The condensation product, prepared at about 160° C., is said to be "predominantly, if not exclusively, an amide" and is assertedly of the formula R—CO—NR$_1$—CH$_2$—(CHOH)$_4$—CH$_2$OH wherein R is an alkyl radical containing at least 3 carbon atoms, while R$_1$ is hydrogen or an alkyl radical.

U.S. Pat. No. 2,016,962, issued Oct. 8, 1935, discloses a process for preparing glucamines and related products.

U.S. Pat. No. 2,703,798, Schwartz, issued Mar. 8, 1955, asserts that compositions produced by reacting fatty acids or acid anhydrides with N-alkylglucamines (presumably such as the process as taught by Piggott) have poor color and poor detergency properties. Thus, Schwartz teaches problems associated with forming the condensation products of N-monoalkylglucamines and fatty acids, with respect to undesirable color characteristics and detergency properties.

According to Schwartz, approximately equimolar proportions of N-monoalkylglucamines can be reacted with fatty alkyl esters by heating at 140° C.–230° C., preferably 160° C.–180° C. at normal, reduced or superatmospheric pressures for a period "somewhat in excess of one hour" during which time two initially immiscible phases merge to form a product said to be a useful detergent.

Suitable N-monoalkylglucamines are illustrated by N-methylglucamine, N-ethylglucamine, N-isopropylglucamine and N-butylglucamine. Suitable fatty alkyl esters are illustrated by the product of reacting a $C_6$–$C_{30}$ fatty acid with an aliphatic alcohol, e.g., methyl ester of lauric acid.

More recent processes include those described in U.S. Pat. No. : 5,334,764, Schiebel, Connor, Shumate, and St. Laurent; U.S. Pat. No. 5,338,486, Connor, Scheibel, and Kao; U.S. Pat. No. 5,338,487, Connor, Scheibel, and Kao; and U.S. Pat. No. 5,380,892, Connor, Scheibel, and Kao, all of said patents being incorporated herein by reference.

According to Thomas Hedley & Co. Ltd. (now Procter & Gamble Ltd.), British Pat. No. 809,060 published Feb. 18, 1959, the compounds made by the process herein are useful as surfactants for laundry detergents such as those having granular form. Hildreth (supra) mentions use of the compounds herein in the biochemistry field as detergent agents for solubilizing plasma membranes and EP-A 285,768, published Dec. 10, 1988, describes application of these compounds as a thickener. Thus, these compounds, or compositions containing them, can be highly desirable surfactants.

Yet another process for making compositions comprising the amide compounds of this invention is included in the above-identified disclosure of improved thickeners. See EP-A 285,768. See also H. Kelkenberg, Tenside Surfactants Detergents 25 (1988) 8–13, inter alia for additional disclosures of processes for making N-alkylglucamines. All of the above patents and publications are incorporated herein by reference.

SUMMARY OF THE INVENTION

The present development relates to a series of improvements relating to processes for preparing amides of N-alkyl polyhydroxy amines (N-alkylamino polyols). Both the N-alkyl polyhydroxy amines and the source of fatty acyl groups, e.g., esters, used to form the amides are selected to have good color; the reaction conditions are selected to avoid the formation of color materials and precursors for color materials; and/or the amide product is treated with an ion exchange resin, mixtures of ion exchange resins, or combinations thereof, and/or a reducing "bleach" to prepare the best color amides. The combination of all of the improvements is required in order to achieve amides with the very best color for formulating detergent compositions, especially liquid detergent compositions that are "water white" and which contain low levels of cyclic materials.

The invention provides a process for preparing polyhydroxy fatty acid amide surfactants, comprising reacting a member selected from the group consisting of fatty acids, fatty acid anhydrides and fatty acid esters, especially fatty acid esters, having greater than 98% transmittance at 460 nm with an N-alkylamino polyol having a Gardner Color of less than 1 (<0.1 absorbence at 440 nm), e.g., methyl esters or triglycerides. Crystallization of said N-alkylamino polyol can be used to provide the appropriate purity and color. N-alkylamino polyol with this Gardner Color is "stable" for three hours at 130° C. The N-alkylamino polyol is considered stable if it has a Gardner Color of 4, or less, after three hours under these conditions. A less pure N-alkylamino polyol will be a dark brown after three hours under these conditions. Also, in order to prepare the best color amides, the dehydration of N-alkylamino polyol should be carried out at between about 110° C. and about 160° C. for a period of time of less than about three hours, more preferably at a temperature of from about 120° C. to about 140° C. for a period of time of less than about one and a half hours and even more preferably at a temperature of from about 130° C. to about 135° C. for a period of time of less than about one hour. However, for commercial practice, good results can be obtained with dehydration times of from about four to about eight hours, preferably from about five to about six hours, to accommodate commercial equipment limitations. A more pure N-alkylamino polyol can be achieved by crystallization from an aqueous solution, either with, or without, an organic solvent present.

The dehydrated N-alkylamino polyol is then reacted with, e.g., fatty acid esters and especially triglycerides, to form fatty acid polyhydroxy amide surfactants.

The resulting polyhydroxy fatty acid amide surfactant is then post treated with an ion exchange resin, mixture of ion exchange resins, or combinations of ion exchange resins, and/or reducing bleach such as $NaBH_4$, etc., or hydrogenation over a catalyst, as taught hereinafter, and, optionally, combinations of treatments. A particularly effective post treatment is the hydrogenation of a solution of the polyhydroxy fatty acid amide surfactant over a hydrogenation catalyst like nickel, palladium, copper chromite, etc.

In a preferred process, the fatty acid ester is a $C_{10}$–$C_{18}$ alkyl or alkenyl fatty acid methyl ester, or, triglyceride, and the N-alkylamino polyol is selected from N-methyl glucamine, N-methyl fructamine, N-methyl maltamine and N-methyl glycerolamine.

DETAILED DESCRIPTION OF THE INVENTION

The processes of this invention employ selected reactants, N-alkylamino polyols and sources of fatty acyl groups, with good color, especially color that is heat stable.

The "color" referred to herein is the Gardner Color, e.g., of the N-alkylamino polyol, the N-alkylamino fatty acid amide, etc. "Gardner Color" is the standard Gardner measurement known in the art. A Gardner Color reading near zero (solution) represents a nearly colorless ("water-white") solution. Gardner Colors below about 1 are required for the N-alkylamino polyol reactants, and it is preferred to have Gardner Colors close to 0.

Gardner Color is determined by A.O.C.S. (American Oil Chemists Society) Official Method to 1a-64, entitled COLOR Gardner 1963 (Glass Standards) established 1978 and revised 1982. The equipment and standards for determining Gardner Color can be purchased from Delta Scientific, Box 5728, Long Island, N.Y. 20014, or from Gardner Laboratory, Silver Spring, Md., U.S.A. As used herein, the Gardner Color limits typically refer to the color resulting from the color bodies that are present, or which are the result of the described reactions, and not to deliberately added color materials.

The odor characters of the N-alkylamino polyol reactant, and its amide, are substantially free of amine or "fish" type odor (once any excess N-alkylamine is removed) and also substantially free of typical browning sugar odors.

The N-alkylamino Polyols

Suitable N-alkylamino polyols can be prepared by processes similar to those described in U.S. patent application Ser. No. 07/907,382, filed Jul. 8, 1992, now abandoned, in the name of Junan Kao et al. for PROCESS FOR PREPARING N-ALKYLAMINES IN AQUEOUS/HYDROXY SOLVENTS, said application being incorporated herein by reference, especially page 6, line 4, to page 23, line 3 and EXAMPLES I–VI, and IX–XIV. The polyhydroxy amine used to form the polyhydroxy acid amide can be made by any process that will provide the desired color.

As discussed hereinafter, N-alkylamino polyols with good color are achieved by careful selection of reaction conditions.

The reaction for the preparation of the N-alkylamino polyols (also referred to herein as "polyhydroxyamines" or "N-alkyl polyhydroxy amine") herein can be termed the "R-1" reaction, and is illustrated by the formation of N-methylglucamine, wherein $R^1$ is methyl.

Adduct Process

In this first variation of the R-1 reaction, the process involves pre-reacting the amine and reducing sugar to form an adduct.

water and/or organic solvent, e.g., methanol
$R^1NH_2 + glucose \rightarrow Adduct + H_2O$ The Adduct has the formula (I) as follows:

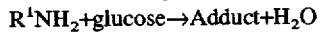
$R^1NH-CH-(CHOH)_3-CH-CH_2OH$

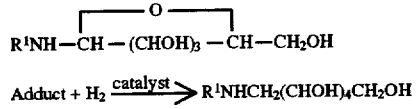

The reactants, solvents and catalysts used in the R-1 reaction are all well-known materials, although not usually used in such purified form for making detergent surfactants, and are available, at least in some form, from a variety of commercial sources. The following are nonlimiting examples of materials which can be used herein.

Amine Material - The "N-alkylamines" used to form the N-alkylamino polyols include primary amines of the formula $R^1NH_2$, wherein $R^1$ is, for example, alkyl, e.g., $C_1$–$C_{18}$, especially $C_1$–$C_4$ alkyl, or the corresponding hydroxyalkyls, e.g., $C_1$–$C_4$ hydroxyalkyl. Examples include methyl, ethyl, propyl, hydroxyethyl, and the like. Nonlimiting examples of amines useful herein include methyl amine, ethyl amine, propyl amine, butyl amine, 2-hydroxypropyl amine, 2-hydroxymethylpropyl, 2-hydroxyethyl amine; 1-methoxypropyl, and methyl amine. The $C_1$–$C_3$ alkylamines are preferred, and N-methylamine is most preferred. All such amines are jointly referred to herein as "N-alkyl amines." The amine can be either anhydrous or in a solvent, e.g., aqueous solvent, of a concentration of from about 30% to about 90%, preferably from about 40% to about 70%.

Polyhydroxy Material - A preferred source of polyhydroxy materials useful in all of the R-1 reactions comprise reducing sugars or reducing sugar derivatives. By "sugars" herein is meant reducing sugars such as glucose, fructose, mannose, lactose, maltose, xylose and the like. The term "sugars" herein also includes glyceraldehyde. Such "sugars" can include materials which break down to form sugars, such as plant syrups such as cane syrups, corn syrups, potato starch-derived sugar syrups, hydrolyzed wood pulp-derived sugars and the like. High fructose, high glucose and high maltose syrups are economical and preferred, especially if their Gardner Color is satisfactory. The reactant sugar material comprises, for this first variation, an adduct with the amine such as methylamine. The species are determined (measured) by g.c. analysis, (gas-liquid chromatography or "g.l.c.") using Hewlett-Packard 5890 Series 2 on column injection using DB1 15 meter 0.25 m film thickness ID 250 m.

A particular advantage of the "Adduct" process is that the "Adduct" can be formed in the presence of water. Accordingly, raw materials such as corn syrup, and the like, can be used as the sugar source. However, the sugar solution can be prepared from granular, powdered, etc., sugar by dissolving the sugar in the solvent, preferably aqueous solvent. Concentrations of sugar in the solvent, e.g., water, are typically from about 40% to about 90%, preferably from about 50% to about 70% (Typically, 71% is the upper limit.) It is highly important that the color of the starting sugar material, for preparing all N-akylamino polyols, be less than about one on the Gardner Color scale, preferably less than about Gardner 0+, and more preferably about water white. Typical color materials that are present in the starting sugar materials negatively affect the catalyst and the reaction yield. These color materials also contribute to the eventual color of the N-alkylamino polyols. Such colors can be removed, if present, by procedures such as "carbon bleaching," in which the color materials are adsorbed. The sugar material is preferably handled without excessive heating and/or under non-oxidizing conditions to prevent degradation.

Of course, use of sugars having low Gardner Colors (e.g., 0 or <1, i.e., water-white syrups) to form the N-alkylamino polyols will help ensure that N-alkylamino polyols having desirably low Gardner Colors will be produced. Stated otherwise, use of low (0–1) Gardner Color sugars (preferably white solids or water-white solutions) and use of the reaction sequence disclosed herein results in low Gardner Color N-alkylamino polyols.

Catalyst - A variety of hydrogenation catalysts can be used in the R-1 reaction. Included among such catalysts are nickel (preferred when treated as discussed hereinafter), platinum, palladium, iron, cobalt, tungsten, various hydrogenation alloys, and the like. The catalyst used in the hydrogenation step is preferably a particulate nickel catalyst, Raney nickel, nickel, other nickel catalysts affixed to substrate materials such as silica or alumina. Catalysts which are easier to remove (e.g., by filtration) are preferred. Highly preferred catalysts herein comprise "United Catalyst G49B," "United Catalyst G96," and "UCI C46" particulate Ni catalysts supported on silica, available from United Catalysts, Inc., Louisville, Ky, and Raney nickel type catalysts from W. R. Grace & Co., of Baltimore, Md., such as RA4200 and RA3100.

Achieving good color also requires optimizing and maintaining the activity of the preferred nickel catalysts including any of the conventional Raney nickel or "supported" nickel catalysts well-known in the art. Conventional nickel under the trademark RANEY NICKEL 4200 and 3200 (Grace Chemicals) are quite suitable for use herein. UCI (United Catalyst, Inc.) G-96B and G-49B and G-49C are also suitable. With respect to the nickel catalyst, it is believed that removing oxides of nickel from the catalyst prevents or impedes dissolution of nickel ions into the reaction milieu, and thus results in the formation of reaction products having a desirable low nickel content. Moreover, it has been found that the nickel catalyst pre-treated and preferably post-treated with pressurized hydrogen can be re-used in multiple subsequent reactions, thereby yielding a substantial overall cost savings. In general, nickel catalysts, such as those that are commercially available, typically are contaminated with, e.g., oxides of nickel, organic materials, excess caustic, and/or alumina fines, especially after shipping and storage. The nickel catalysts that are used in the processes herein are preferably free of catalytic activity inhibiting quantities of nickel oxides, organic materials, caustic, alumina fines, etc. Therefore, it is desirable to wash the catalyst with one, or more, solvents to effect removal of organics and/or water-soluble materials, to preferably lower the pH, and/or treat the catalyst with a strong reducing agent, e.g., hydrogen gas under high pressure and/or temperature conditions, to destroy, or remove, the nickel oxides. Once the catalyst is "cleaned," the catalyst is desirably maintained under non-reactive atmosphere, e.g., nitrogen gas, or, more desirably, a reducing gas, e.g., hydrogen. Any exposure to the normal atmosphere should desirably occur for only short periods of time and while the temperature is low. The activity of the catalyst can be increased substantially by the reduction, or removal, of these impurities, even when they are present in very small amounts. The resulting catalyst also provides amines, and therefore amides, with good color.

When the nickel catalyst is in contact with either adduct or N-alkyl polyhydroxyalkyl amine, the hydrogen pressure should be maintained to minimize catalyst solubilization. Similarly, a high hydrogen pressure, e.g., from about 100 psig to about 3500 psig, preferably from about 500 psig to about 1500 psig, and a temperature of from about 20° C. to about 135° C., preferably from about 40° C. to about 85° C., will reduce the level of nickel ion dissolved in the N-alkyl polyhydroxyalkyl amine, and, by depositing the nickel back onto the catalyst, regenerate its activity.

A combination of hydrogen gas and selected pressure/temperature conditions can reduce this solubilization and, in fact, reverse the process to deposit nickel and regenerate the catalyst. Lowering the soluble Ni content in the N-alkyl polyhydroxy amine product to less than about 10 ppm, preferably less than about 5 ppm, more preferably less than about 2 ppm, will effectively regenerate the catalyst.

When the catalyst is separated from the N-alkyl polyhydroxyalkyl amine, the temperature should be less than about 135° C., preferably less than about 85° C., and the separation, typically filtration, should be accomplished under hydrogen pressure.

Regeneration of catalyst can be achieved using the step described for initial activation.

The N-alkylamino polyol reactant herein, which is "substantially free of nickel", contains no more than about 20 parts per million (ppm) nickel, and preferably less than about 5 ppm nickel (Ni++). Nickel can be conveniently measured by conventional atomic absorption spectroscopy, using diluted samples (5/1 dilution to minimize interference).

Solvent - Formation of the adduct in the R-1 process is conveniently carried out in water and/or organic solvent, especially polar, most preferably hydroxy solvents. Typical examples of organic solvents useful herein in the formation of the amine-sugar adduct include methanol (preferred), ethanol, 1-propanol, iso-propanol, the butanols, ethylene glycol, 1,2-propylene glycol (preferred), 1,3-propylene glycol, glycerol and the like. The amine itself can also function as a solvent, typically at mole ratios of amine:sugar of from about 4:1 to about 30:1.

The hydrogenation reaction of the R-1 reaction can also be carried out in the presence of an organic or aqueous solvent which dissolves the adduct. Hydrogenation solvents are, conveniently, polar, especially hydroxy, solvents, i.e., of the same type as those mentioned above for use in the formation of the adduct. When substantially anhydrous organic solvent is used, the unreacted amine is removed with the water after the adduct formation step. However, when an aqueous solvent is used, the amine and solvent are not removed until the catalyst removal step.

Water is the preferred solvent for the hydrogenation reaction. Methanol is a preferred organic solvent for use in the hydrogenation reaction.

General R-1 Reaction Conditions - Reaction conditions for the R-1 reaction are as follows.

Step (a) - Adduct formation - Step (a) of the process is preferably carried out at a temperature of from about 0° C.

to about 80° C., preferably from about 10° C. to about 60° C., for processes utilizing organic hydroxy solvent and below about 70° C., preferably less than about 50° C., more preferably less than about 30° C., more preferably from about 15° C. to about 25° C., for aqueous solvents.

The reaction time used for adduct formation will typically be on the order of from a few minutes to about 20 hours, depending somewhat on the reaction temperature chosen and/or the ratio of amine to sugar. In general, for the organic solvent, lower reaction temperatures in the range of 0° C.–80° C. require longer reaction times, and vice-versa. In general, for the organic solvent, over a preferred 10° C.–60° C. reaction temperature range, good adduct yields, e.g., more than about 90%, preferably more than about 95%, are achieved in 1-10 hours for the organic solvent. For the lower reaction temperature range, 0°–70° C., preferably 0°–30° C., that gives good color, especially in water, the reaction time can also be as much as 10 hours, but, typically, equilibrium is substantially reached within about four hours or less, especially with higher amine:sugar ratios. The temperature and reaction time are selected to give an adduct with a Gardner Color of preferably less than about 1. Good adduct color is necessary for obtaining good reactions and color in any subsequent hydrogenation reaction and maintaining catalyst activity. Below a Gardner Color of about 1, the resulting N-alkyl polyhydroxy amine, and consequently the resulting amide, has good color. The color bodies can be removed by, e.g., carbon bleaching as used for the sugar solution.

The adduct also has a very low level of glucose. The glucose level, as a percentage of the adduct is preferably less than about 1%, and more preferably less than about one-half of one percent. Glucose interferes with the hydrogen reaction step to form the N-alkyl polyhydroxy amine. Excess amine can also help reduce the glucose level and minimize formation of sorbitol during hydrogenation.

In general, the temperature will rise during adduct formation since the reaction is exothermic. Therefore, maintaining temperatures below about 30° C., as required in batch processes, involves providing cooling for the reactants and/or the reaction mix. Temperatures above about 50° C. require reaction times of less than about 10 minutes to avoid excessive color formation. Such short times are normally not feasible except in a continuous reaction. Even with such a continuous reaction, back-mixing should be minimized, e.g., by use of plug flow conditions, to avoid excessive exposure of the adduct to higher temperatures. Ideally, the adduct is promptly reacted with hydrogen to form the corresponding N-alkyl polyhydroxy amine to minimize degradation. However, temperatures below about 30° C., preferably less than about 20° C., allow one to handle and/or store the adduct for at least several hours, which facilitates the use of batch processes. At 0° C., the adduct is stable for 24 hours.

Surface temperatures, e.g., when preheating the adduct for the hydrogen reaction process, should be maintained below about 100° C., preferably below about 70° C.

Reactant concentrations can vary. Molar ratios of amine:sugar not greater than about 7:1 are preferably used herein, although ratios up to about 30:1 can be used when the amine is used as a solvent, at least in part. Generally the desired adduct formation is achieved at a mole ratio of amine:sugar with an excess of amine, e.g., mole ratios of >1:1, preferably greater than about 1.1:1, and the like, e.g., greater than about 1.3:1. Typical reactant concentrations in the water and/or hydroxy solvent are in the 10–80%, typically 40–50% (wt.) range. Adduct formation can be carried out at atmospheric or superatmospheric pressures.

Step (b) Reaction with Hydrogen - Step (b) should be accomplished so as to avoid the prolonged exposure of the adduct to the catalyst when the hydrogen pressure is less than about 500 psig, and preferably the hydrogen pressure should be at least about 1000, and more preferably at least about 1500 psig. Keeping this time below about one hour, and preferably below about a half hour, minimizes the amount of catalyst metal, e.g., nickel, that is converted to water soluble ion. Such ions are undesirable for a variety of reasons including their affect on color formation, incompatibility with other materials, safety, etc.

Step (b) can be carried out in either a slurry process or a fixed bed. Step (b) is preferably carried out at a temperature of from about 20° C. to about 120° C., preferably from about 50° C. to about 100° C. for organic hydroxy solvent processes. Step (b) is preferably carried out in two stages for aqueous solvent processes. The first stage is at a temperature that is low enough to avoid formation of the corresponding reduced sugar, e.g., sorbitol in the case of glucose, and other unwanted byproducts. Typically this is from about 20° C. to about 70° C., more preferably from about 40° C. to about 65° C., and even more preferably from about 50° C. to about 60° C. In the second stage, after the reduction (hydrogenation) of the adduct to the N-alkyl polyhydroxy amine is at least about 80% complete, preferably at least about 90% complete, more preferably at least about 95% complete, the temperature is raised to at least about 75° C., preferably at least about 80° C., and up to about 135° C., preferably 130° C., so that the remaining adduct and any other materials that may form color bodies are minimized and the adduct is at least about 95%, preferably at least about 98%, more preferably at least about 99.9% converted to the corresponding N-alkyl amino polyol. This second stage is essential to the preparation of N-alkyl polyhydoxy amine with good stable color upon heating. Heat stability is improved for the N-alkylamino polyol by using excess amine in the preparation step and a higher temperature at the heat treatment step.

During Step (b) it is highly preferred to avoid localized overheating, e.g., at the surface of the heating element or heat exchanger. Such surface or "skin" temperatures should be below about 180° C., preferably below about 100° C., and even more preferably less than about 70° C., during the first stage and less than about 100° C. during the second stage.

The reaction with hydrogen is preferably carried out with limited initial water when the solvent is an organic hydroxy solvent, although even then, water (e.g., up to 1:1 wt. $H_2O$:alcohol) can be present. Optional water removal from the adduct prepared in Step (a) can be effected by use of drying agents, or by simply stripping water and solvent from the adduct, and then redissolving the adduct in fresh water-free solvent. The hydrogen reaction can typically be run, for example, at temperatures of 20° C.–120° C. at 50–1,000 psi or, for example, at 50° C.–90° C. at 100–500 psi for periods of 0.1–35 hours, generally 0.5–8 hours, typically 1–3 hours when the organic solvent is used.

When the solvent comprises water, the hydrogenation reaction is done in two stages as discussed before.

The adduct/solvent solution used in the hydrogen reaction is typically at a 10–80%, typically 40–50%, (wt.) solute level.

It will be appreciated that the selection of hydrogen reaction conditions will depend somewhat on the type of pressure equipment available to the formulator, so the above-noted reaction conditions can be varied without departing from this invention. However, as noted before, the hydrogen pressure preferably should be above about 500, preferably 1000, more preferably about 1500, psig when the adduct and the catalyst, especially the preferred nickel catalyst, are both present. Use of lower pressures down to about 100 psig will require either a separate step to remove Ni ion, or more prolonged post treatment, as discussed hereinafter, to achieve very low Ni content.

Hydrogen reaction catalyst levels are typically from about 1% to about 100%, preferably from about 2% (preferably about 5%) to about 30% (preferably 20%) more preferably from about 5% (preferably 10%) to about 15% (preferably about 20%) solids by weight, calculated based on wt. catalyst:wt. reducing sugar substituent.

Step (c) Finishing - The catalyst is then separated from the product after the reaction is completed. The catalyst is removed from the product of Step (c) which is then preferably dried by crystallization, or by solvent/water stripping, or by means of effective drying agents. This helps prevent reversion to the sugar starting material.

Step (c), when it involves solvent/water stripping, is preferably done in a wiped film evaporator.

Steps (a)-(c) of the R-1 process are preferably conducted under non-oxidizing conditions (e.g., $H_2$ or inert gas) to provide good color. Catalyst removal in the Step (c) process is done preferably under hydrogen pressure to prevent Ni (catalyst) dissolution or at least under inert conditions.

Glucose Addition Process

Another suitable process for preparing the polyhydroxy amine utilizes glucose addition (The "Glucose Addition" process) after premixing the catalyst and amine in a simplified reaction which can achieve good results so long as the glucose is added under a hydrogen pressure of at least about 100 psig, preferably at least about 500 psig, and more preferably at least about 1000 psig, at a temperature of less than about 80° C., preferably less than about 70° C., most preferably less than about 60° C. The materials and the conditions for the remainder of the reaction are the same as detailed above for the adduct process.

The preparation of the N-alkylaminol polyols by either of the processes can be conducted in any well-stirred pressure vessel suitable for conducting hydrogenation reactions. In a convenient mode, for the "Glucose Addition" process, a pressure reactor with a separate storage reservoir is employed. The reservoir (which, itself, can be pressurized) communicates with the reactor via suitable pipes, or the like. In use, a stirred slurry of the nickel catalyst is first "cleaned," including being treated with hydrogen to remove traces of nickel oxides. This can be conveniently done in the reactor. (Alternatively, if the manufacturer has access to an oxide-free source of nickel catalyst, pretreatment with $H_2$ is unnecessary. However, for most manufacturing processes some trace of oxides will inevitably be present, so the $H_2$ treatment is preferred.) After removal of excess slurry medium (water) the N-alkyl amine is introduced into the reactor. Thereafter, the sugar is introduced from the storage reservoir into the reactor either under hydrogen pressure or by means of a high pressure pumping system, and the reaction is allowed to proceed. The progress of the reaction can be monitored by periodically removing samples of the reaction mixture and analyzing for unreacted sugar using gas chromatography ("g.c"), or by heating the sample to about 100° C. for 30–60 minutes in a sealed vial to check for color stability. Typically, for a reaction of about 8 liters (ca. 2 gallons) size the initial stage (to 95% of reducibles being depleted) requires about 60 minutes, depending somewhat on catalyst level and temperature. The temperature of the reaction mixture can then be raised to complete the reaction (to 99.9% of the reducibles being depleted).

Crystallization of Polyhydroxyamines

The color quality, stability, and/or purity of the N-alkylamino polyol can be further improved by a process of crystallization of the N-alkylamino polyol from an aqueous solution or water/organic solvent mixture. Crystallization is carried out by cooling the aqueous mixture of the N-alkylamino polyol from Step (b) to 0°–10° C., or more, preferably by concentrating the aqueous mixture to about 70% solids prior to cooling, and most preferably by adding from about 10 to about 200 parts of an organic solvent, e.g., methanol, acetone, etc. either to the aqueous feed solution, or, most preferably, to the concentrated solution. Highly pure crystals of the N-alkylamino polyol form which can be isolated from the supernatant solution by filtration and/or centrifugation. To obtain the purest crystals possible, the filter cake, or centrifuge cake, should be washed with from about 0.25 to about 1.25 parts of chilled (0°–5° C.) solvent. The wet cake can then be employed to produce polyhydroxy fatty acid amides with reduced color. The crystallization method provides a surprisingly improved amide product.

Formation of Polyhydroxy Fatty Acid Amides

The N-alkylamino polyol compounds prepared by either of the above reactions and having the required Gardner Color can be used in an overall process for preparing polyhydroxy fatty acid amide surfactants which includes an amide-forming reaction comprising reacting a source of fatty acyl groups such as fatty acids, fatty acid anhydrides and fatty acid esters, especially fatty acid esters, having greater than 98% transmittance at 460 nm with an N-alkylamino polyol having a Gardner Color of less than 1 (<0.1 abs. at 440 nm), more preferably esters which have been distilled in the presence of from about 0.05% to about 2% alkali metal oxide, e.g., those prepared in the foregoing manner, in an organic hydroxy solvent in the presence of base catalyst. The formation of such surfactants with high purity and low color is an especially beneficial result of such a process when an organic hydroxy solvent is used, since the detergent formulator can pump and/or incorporate the polyhydroxy fatty acid amide reaction product plus the reaction solvent such as 1,2-propane diol, (propylene glycol), glycerol, or alcohol (e.g., in liquid detergents) directly into the final detergent formulation. This offers economic advantages in that a final solvent removal step is rendered unnecessary, particularly where anhydrous glycols or ethanol are used.

The polyhydroxyamine products of either of the aforesaid R-1 reactions, preferably with water substantially removed, can be further employed in an amide-forming reaction which is designated herein as the "R-2" reaction. A typical R-2 amide-forming reaction herein can be illustrated as follows:

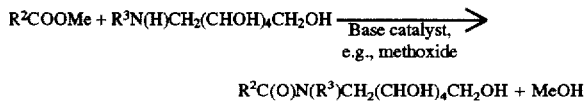

$R^2C(O)N(R^3)CH_2(CHOH)_4CH_2OH + MeOH$ wherein each $R^2$ is $C_{10}$–$C_{20}$ alkyl and each $R^3$ is $C_1$–$C_4$ alkyl, $C_1$–$C_4$ alkoxyalkyl, or hydroxyalkyl group.

Thus, the process herein can encompass an overall process for preparing polyhydroxy fatty acid amide surfactant optionally comprising an R-1 process as described above and then reacting the polyhydroxyamine having a color of less than Gardner 1 with a fatty acid ester having at least 98% transmittance at 460 nm in an organic hydroxy solvent (preferably, methanol) in the presence of a base catalyst to form the polyhydroxy fatty acid amide surfactant (at a temperature of from about 40° C. to about 135° C. for a time of less than about three hours, more preferably at a temperature of from about 40° C. to about 100° C., and even more preferably at a temperature of from about 50° C. to about 80° C. for a time of less than about 2 hours,); and optionally, removing said solvent. The resulting amide product is treated with ion exchange resin, more preferably a mixture of acid and base resins, or, optionally, with reducing bleach to provide a product that is essentially "water white".

In a more preferred embodiment, the amide surfactant is treated first with acid ion exchange resin to convert any soap to fatty acid and remove any residual amine that has not been converted to amide. Then the amide surfactant is treated with base ion exchange resin to remove the fatty acid. Both resins remove part of any color bodies that have already formed.

R-2, or the combination of R-1 and R-2 reactions herein, can be used to prepare polyhydroxy fatty acid amide suffactants of the formula (II) as follows:

$R^2$—C(O)—N($R^1$)—Z wherein: each $R^1$ is H, $C_1$–$C_4$ hydrocarbyl, $C_1$–$C_4$ alkoxyalkyl, or hydroxyalkyl, e.g., 2-hydroxyethyl, 2-hydroxypropyl, etc., preferably $C_1$–$C_4$ alkyl, more preferably $C_1$ or $C_2$ alkyl, most preferably $C_1$ alkyl (i.e., methyl) or methoxyalkyl; and $R^2$ is a $C_5$–$C_{31}$ hydrocarbyl moiety, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof, and Z is a polyhydroxyhydrocarbyl moiety having a linear hydrocarbyl chain with at least 3 hydroxyls directly connected to the chain, or an alkoxylated derivative (preferably ethoxylated or propoxylated) thereof Z preferably will be derived from a reducing sugar in a reductive amination reaction; more preferably Z is a glycityl moiety. Z preferably will be selected from the group consisting of —$CH_2$—(CHOH)$_n$—$CH_2OH$, —CH($CH_2OH$)—(CHOH)$_n$—$CH_2OH$, —$CH_2$—(CHOH)$_2$(CHOR')(CHOH)—$CH_2OH$, where n is an integer from 3 to 5, inclusive, and R' is H or a cyclic mono- or poly- saccharide, and alkoxylated derivatives thereof. Most preferred are glycityls wherein n is 4, particularly —$CH_2$—(CHOH)$_4$—$CH_2O$. Mixtures of the above Z moieties are desirable.

In Formula (II), $R^1$ can be, for example, N-methyl, N-ethyl, N-propyl, N-isopropyl, N-butyl, N-isobutyl, N-2-hydroxyethyl, N-1-methoxypropyl, or N-2-hydroxypropyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The following reactants, catalysts and solvents can conveniently be used in the R-2 reaction herein, and are listed only by way of exemplification and not by way of limitation. Such materials are all well known and are routinely available from a variety of commercial sources.

Reactants - Various fatty esters can be used in the R-2 reaction, including mono-, di- and tri-esters (i.e., triglycerides). Methyl esters, ethyl esters, and the like are all quite suitable. The polyhydroxyamine reactants include reactants available from the above-described R-1 reaction, such as N-alkyl and N-hydroxyalkyl polyhydroxyamines with the N-substituent group such as $CH_3$—, $C_2H_5$—, $C_3H_7$—, $HOCH_2CH_2$—, and the like. (Polyhydroxyamines available from the R-1 reaction are preferably not contaminated by the presence of residual amounts of metallo hydrogenation catalysts, although a few parts per million [e.g., 10–20 ppm] can be present.) Mixtures of the ester and mixtures of the polyhydroxyamine reactants can also be used.

Catalysts - The catalysts used in the R-2 reaction are basic materials such as the alkoxides (preferred), hydroxides (less preferred due to possible hydrolysis reactions), carbonates, and the like. Preferred alkoxide catalysts include the alkali metal $C_1$–$C_4$ alkoxides such as sodium methoxide, potassium ethoxide, and the like. The catalysts can be prepared separately from the reaction mixture, or can be generated in situ using an alkali metal such as sodium. For in situ generation, e.g., sodium metal in the methanol solvent, it is preferred that the other reactants not be present until catalyst generation is complete. The catalyst typically is used at a level of about 5–8 mole % of the ester reactant. Mixtures of catalysts can also be used.

Solvents -The organic hydroxy solvents used in the R-2 reaction include, for example, methanol, ethanol, propanol, iso-propanol, the butanols, glycerol, 1,2-propylene glycol, 1,3-propylene glycol, and the like. Methanol is a preferred alcohol solvent and 1,2-propylene glycol is a preferred diol solvent. Mixtures of solvents can also be used.

General R-2 Reaction Conditions - It is also an optional objective herein to prepare the desired products while minimizing the formation of cyclized by-products,

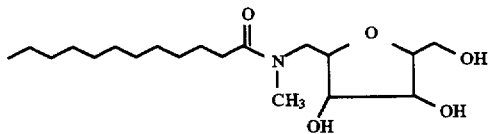

e.g., ester amides and color bodies. Reaction temperatures below about 35° C., typically in the range of from about 40° C. to about 100° C., preferably 50° C. to 80° C., are used to achieve this objective, especially in batch processes where reaction times are typically on the order of about 0.5–2 hours, or even up to 6 hours. Somewhat higher temperatures can be tolerated in continuous processes, where residence times can be shorter.

Purification of the Polyhydroxy Fatty Acid Amide

The polyhydroxy fatty acid amide surfactant prepared by the processes herein is very pure and has good color. However, for products that are not colored, or which are clear, even purer, less colored surfactants are required. Accordingly, the polyhydroxy fatty acid amide surfactant is preferably post treated with an ion exchange resin, mixture of ion exchange resins, or combinations of ion exchange resins, and/or reducing bleach such as $NaBH_4$, etc., or hydrogenation over a catalyst.

Treatment with ion exchange resins can be very effective if the treatment is carefully carried out. Since the minor contaminants present are both cationic in nature, e.g., amines, and/or artionic in nature, e.g., soaps and/or fatty acids, it is desirable to treat with both anionic and cationic (acidic and basic) ion exchange resins. A particularly effective treatment is to treat a solution of the polyhydroxy fatty acid amide surfactant first with acid ion exchange resin to remove the amine and convert any fatty acid soap to fatty acid and then treat with base ion exchange resin to remove the fatty acid.

Another particularly effective post treatment is the hydrogenation of a solution of the polyhydroxy fatty acid amide surfactant over a hydrogenation catalyst like nickel, palladium, copper chromite, etc. Surprisingly, the hydrogenation is effective in eliminating color bodies and color body precursors without adversely affecting the structure of the surfactant.

The hydrogenation is typically carried out in a batch reactor. A catalyst, typically of either nickel or palladium, is slurried in a solution of the polyhydroxy fatty acid amide surfactant and reacted under conditions that will achieve the desired improvement. Typical reaction conditions are hydrogen pressure of from about 150 to about 1000, preferably from about 300 to about 500, psi; temperature of from about 50° to about 120°, preferably from about 50° to about 65, ° C., to limit potential soap formation; and reaction time of from about one to about four, preferably from about one to about two hours.

The color of the surfactant is measured as % transmission at 420 nanometers, against a 50/50 mixture, by weight, of methanol/distilled water blank. The surfactant is diluted to 50% by weight with the blank solution and read in a spectrophotometer. Typical color of commercial production varies from about 55% to about 70% transmission, as measured above. For clear products, the minimum transmission should be at least about 70%.

The catalyst loading to achieve 70% transmission depends on the type of catalyst used, and the desired level of color improvement. For nickel catalysts, the loading ranges from about 2% to about 10%, preferably from about 2% to about 5%, expressed as weight of catalyst based upon the surfactant in solution. These levels of catalyst will raise the transmission from about 40%–48% to about 70% with 2% catalyst and to about 80–85% with 10% catalyst. Post hydrogenation with palladium catalyst produces superior color with less catalyst. Palladium catalyst usage ranges from about 0.005% to about 0.15% with resulting transmissions of from about 85% to about 90% when starting with colors having transmissions of about 60%. For comparison, a transmission of about 42% was raised to about 75% by nickel catalyst and to about 93% by palladium catalyst, using conditions of about 120° C. and about 360 psi hydrogen.

Another optional reductive bleaching step utilizes a reducing material such as; $NaBH_4$, $LiAlH_4$, etc. It has been found that the pH should be from about 10 to about 10.9, preferably from about 10.1 to about 10.6, more preferably about 10.4. This pH range provides excellent bleaching at a good rate without excessive creation of fatty acid soap by hydrolysis of the amide.

The following examples are intended to illustrate the practice of the R-2 reaction using the N-polyhydroxyamines prepared by the above-disclosed R-1 reaction (with $H_2O$ having been removed). It is desirable to use concentration ranges of the reactants and solvent to provide a "70% concentrated" (with respect to reactants) reaction mixture. This 70% concentrated mixture provides excellent results, in that high yields of the desired polyhydroxy fatty acid amide product are secured rapidly. Indeed, indications are that the reaction is substantially complete within one hour, or less. The consistency of the reaction mixture at the 70% concentration level provides ease of handling. However, even better results are secured at the 80% and 90% concentration levels, in that chromotography data indicate that even less of the undesired cyclized by-products are formed at these higher concentrations. At the higher concentrations the reaction systems are somewhat more difficult to work with, and require more efficient stirring (due to their initial thickness), and the like, at least in the early stages of the reaction. Once the reaction proceeds to any appreciable extent, the viscosity of the reaction system decreases and ease of mixing increases.

All percentages, ratios and proportions herein are by weight, unless otherwise specified. All limits and numerical values herein are approximate unless otherwise stated.

EXAMPLE I

Standard Reaction

A reaction mixture consisting of about 214 g $C_{12}$ fatty acid methyl ester (Procter & Gamble methyl ester CE1295); about 195 g N-methyl-D-glucamine, dry powder; about 10.8 g 25% sodium methylate; and about 37.7 g propylene glycol as a solvent is used. The reaction vessel comprises a one liter, four neck, round-bottom flask reactor; one 300 mm coiled condenser; one 250 ml round-bottom flask; several adaptors; one agitator with a variable speed motor; one mantle connected to a THERM-O-WATCH® for temperature control; and a vacuum water aspirator for vacuum.

The methyl ester is added to the reactor and, with agitation, is heated to about 60° C. The propylene glycol and the N-methyl glucamine (powdered), are added with sufficient agitation to keep the solids suspended. The temperature is raised to about 80° C. and a vacuum of about 100 mmHg abs. is created, if more than about 0.1% moisture is present, to eliminate the moisture. The pressure is raised with nitrogen and the sodium methylate is added. The temperature is set at about 80° C. and the time is set at zero. The pressure is reduced approximately every thirty minutes from, approximately, 500 to 350 to 200 to 100 mmHg. The pressure is again raised with nitrogen and a sample is taken for GC analysis.

The above standard reaction results in about 200–600 ppm cyclic material, which is considered undesirable. In one standard reaction, the level of cyclic is 250 ppm while the percent conversion is 91%; lowering the reaction temperature to about 70° C. lowers the cyclic level to about 80 ppm and the conversion to about 88%; lowering the reaction time to about one hour decreases the cyclic materials to about 50 ppm and the conversion to about 89%; cutting the catalyst level in half reduces the cyclic materials to about 90 ppm and raises the conversion to about 93%; removing the methanol in 30 minutes reduces the cyclic materials to less than about 50 ppm and raises the conversion to about 90%; and reducing the vacuum to a maximum of about 200 mmHg reduces the cyclic materials to about 40 ppm while reducing the conversion to about 87%.

Reducing the time to remove the methanol and reducing the vacuum have the most significant impact on reducing cyclic formation.

Color improvement is obtained by using reactants with better color. The methyl ester and polyhydroxy amine should both have a Gardner color of less than about 1, the amine being the most important. Using an excess of amine in the R-1 reaction, e.g., about 100% excess and/or higher heat treatment temperatures provide improved amine color. Use of a crystallization step improves the color even more.

The amide is preferably treated with an ion exchange resin, or, more preferably, with both anionic and cationic ion exchange resins, to remove color bodies. This treatment is accomplished as follows.

EXAMPLE II

An overall process at the 80% reactant concentration level for the amide synthesis is as follows.

A reaction mixture consisting of about 84.87 g $C_{12}$ fatty acid methyl ester (Procter & Gamble methyl ester CE1270), about 75 g N-methyl polyhydroxyamine per Example I, above, about 1.04 g sodium methoxide and a total of about 39.96 g methyl alcohol (ca. 20% by wt. of reaction mixture) is used. The reaction vessel comprises a standard reflux set-up fitted with a drying tube, condenser and mechanical stirring blade. The N-methylglucamine/methanol is heated with stirring under nitrogen (reflux). After the solution has reached the desired temperature, the ester and sodium methoxide catalyst are added. The reaction mixture is maintained at reflux for about 6 hours. The reaction is essentially complete in about 1.5 hours. After removal of the methanol, the recovered product weighs about 105.57 grams. Chromatography indicates the presence of only traces of undesired ester-amide by-products, and no detectable cyclized by-product.

While the foregoing disclosure generally relates to a solvent-assisted method for preparing N-methyl polyhydroxy amines, such as N-methylglucamine, as well as their fatty acid amide derivatives using fatty methyl esters, it is to be understood that variations are available which do not depart from the spirit and scope of this invention. Thus, reducing sugars such as fructose, galactose, mannose, maltose and lactose, as well as sugar sources such as high dextrose corn syrup, high fructose corn syrup and high maltose corn syrup, and the like, can be used to prepare the polyhydroxyamine material (i.e., to replace glucamine) of the reaction.

Surprisingly, a wide variety of fats and oils (triglycerides) can be used herein in place of the fatty esters exemplified above and can provide an unobvious improvement in the degree of completeness. For example, fats and oils such as soybean oil, cottonseed oil, sunflower oil, tallow, lard, safflower oil, corn oil, canola oil, peanut oil, fish oil, rapeseed oil, and the like, or hardened (hydrogenated) forms thereof, can be used as the source of triglyceride esters for use in the present process. When the triglycerides are used, the reaction proceeds to be closer to completion and there are less by-products to be removed. Specifically, greater than about 95% completion is possible. Preferred triglycerides are palm kernel oil, coconut oil, palm oil, and tallow.

Purification

The surfactants produced by the processes disclosed above are surprisingly pure. However, for preparation of very clear products, even greater purity is required. Therefore, it has been found necessary to treat the surfactant product herein by at least one of treatments selected from the group consisting of reductive bleaching and ion exchange treatments.

Reductive bleaching is well known as a method of reducing/eliminating color bodies and/or color body precursors that are converted to color bodies later by action of light, oxygen, interaction with other materials, etc. However, in order to treat the N-alkyl polyhydroxy amine amide surfactant herein, it is necessary to take precautions to avoid soap formation, as disclosed hereinafter The use of hydrogen and hydrogenation catalyst can also provide good reductive bleaching without excessive soap formation although this technique usually is more complicated and requires special equipment. Preferred hydrogenation catalysts are those described hereinbefore.

It will be appreciated that the manufacture of detersive surfactants from such renewable resources is an important advantage of the present process. The present process is particularly useful when preparing the longer-chain (e.g., $C_{18}$) and unsaturated fatty acid polyhydroxy amides, since the relatively mild reaction temperatures and conditions herein afford the desired products with minimal by-product formation. A pre-formed portion of the polyhydroxy fatty acid amide surfactant can be used to assist initiation of the R-2 amide-forming reaction when triglycerides or the longer-chain methyl esters are used as reactants.

EXAMPLE III

Purification of N-methyl glucamine proceeds as follows.

Approximately 2500 g of aqueous solution containing about 45% by weight commercial grade N-methyl glucamine is charged to a rotary evaporator where it is heated to about 71° C. under about 27.5' of Hg vacuum until about 957 g of condensate is collected corresponding to a solids concentration in the evaporator residue of about 75%. The residue is mixed with about 660 g of anhydrous methanol and cooled rapidly to about 1°–2° C. using an ice bath whereupon N-methyl glucamine crystallizes yielding a white slurry. An approximately 1100 g portion of slurry is charged to a Waring blender where it is mixed for about 3–4 minutes before being filtered using a Büchner funnel. The sample was filtered to dryness before being washed twice with about 165 g aliquots of chilled (about 5° C.) methanol and once with about 330 g of chilled methanol. The final cake yields about 438 g of purified N-methyl glucamine at about 16% volatiles for a yield of about 83% of the solids in the original feed.

The following table illustrates the color and heat stability improvement generated by this procedure. The purified crystals are dissolved in distilled water to yield the same concentration of solids as the original feed. Color is measured on the samples as percent transmittance using a Milton Roy Spectronic 21D spectrometer in an about 21 cm cell at about 420 nm. The samples are also tested for heat stability by subjecting the material to about 180° C. in an oil bath under an inert atmosphere for about 1 hour. The treated samples are re-diluted to about 50% concentration to make up for any water lost during heat treatment and the subsequent colors are read.

| Sample | Original Feed | Purified Crystals |
|---|---|---|
| Initial color | 71.9% T | 94.8% T |
| Color after heat treatment | 18.8% T | 89.0% T |

EXAMPLE IV-A (Amide Preparation with Non-Crystallized Amine)

An aqueous solution (about 332.62 g) of commercial grade N-methyl glucamine containing about 54% by weight solids is charged to a standard one liter reaction flask set up comprising a mechanical stirring blade, condenser and receiver. Over the course of about one hour and twenty minutes, the solution is gradually heated to about 132° C. and the pressure is reduced to about 66 cm Hg vacuum to remove the water which is condensed and collected in the receiver.

To the dried N-methyl glucamine is added about 201.71 g of Procter & Gamble CE-1295 methyl ester and about 37.20 g propylene glycol. After stirring, about 15.01 g sodium methoxide solution (about 25% by wgt. in methanol) and about 14 g methanol are added to the reactor and the time is recorded. The mixture is allowed to cool to about 85° C. as methanol is distilled off under atmospheric pressure. After about 30 minutes no more methanol is visibly distilling so vacuum is slowly applied to the reaction vessel to strip out the remaining methanol and drive the reaction to completion. When the vacuum reaches about 66 mm Hg without excessive foaming the reaction is complete. After breaking the vacuum with nitrogen, about 126.86 g water and about 74.60 g ethanol are added to the mixture. The resulting glucose amide solution is dark yellow in color and measures about 54.9% Transmittance at about 420 nm.

EXAMPLE IV-B (Amide Crystallization with Crystallized Amine)

A reaction mixture consisting of about 121.0 g of purified N-methyl glucamine filter cake from Example III (about 16% volatiles), about 112.1 g of Procter & Gamble CE-1295 methyl ester and about 19.7 g propylene glycol are charged to a one liter reaction vessel equipped with mechanical stirring blade, condenser and receiver. The mixture is heated with stirring to about 80° C. and held under a slight vacuum for about 30 minutes to remove any residual moisture and methanol from the filter cake.

After breaking vacuum with nitrogen, about 8.4 g of about 25% sodium methoxide solution is charged to the reactor and the time recorded. Methanol is allowed to distill off and is collected in the receiver. After about one hour, vacuum is slowly applied to strip out the remaining methanol and drive the reaction to completion. After about two and one half hours target vacuum is achieved and no more methanol is distilling. Vacuum is broken with nitrogen and about 65.1 g distilled water and about 39.5 g ethanol are added to the mixture. The resultant glucose amide solution has a very pale yellow tint and measured about 88.9% Transmittance at about 420 nm.

EXAMPLE V

The regeneration of strong base anionic ion exchange resin after exhaustion by polyhydroxy amide elution is conducted as follows.

Ethanolic HCl solution is prepared by adding about 27.4 g of concentrated (about 36.5 wgt %) HCl to about 972.6 g 3A ethanol.

A dilute caustic solution is prepared by dissolving about 15.3 g of NaOH pellets (assay=about 98%) into about 1484.7 g of distilled water.

About four hundred-fifty ml. of exhausted Amberlite IRA-410 resin is packed in a 500 ml graduated dispensing cylinder and is washed with about one liter warm distilled water to remove residual amide. The resin is washed with about one liter of about 5% ethanolic HCl solution (prepared as described above) to acidify, followed by washing with about one liter of ethanol to complete the removal of fatty acid. The resin is then washed with about one liter of warm distilled water to rehydrate the resin.

The resin is then regenerated by slowly eluting about 1½ liters of about 5% aqueous NaOH solution through the resin. The resin is then washed with distilled water until the pH is about 8.

The regeneration of strong acid cationic ion exchange resin after exhaustion by polyhydroxy amide elution proceeds as follows:

Ethanolic HCl solution is prepared by adding about 27.4 g of concentrated (about 36.5 wgt %) HCl to about 972.6 g 3A ethanol.

About four hundred-fifty ml. of exhausted, Amberlite IR-120 Plus strong acid cationic resin is packed in a 500 ml graduated dispensing cylinder, wrapped in about a 50° C. heating tape and is washed with about one liter warm distilled water to remove the residual amide product. The resin is acidified by eluting about one liter of ethanolic HCl and is then washed with warm distilled water to rehydrate the resin.

Regeneration is completed by slowly eluting an additional liter of about 5% aqueous HCl through the resin. The resin is then washed with distilled water until the pH is approximately 5.

EXAMPLE VI

About two hundred mls of regenerated Amberlite IR-120 Plus from Example VII is packed in about a 250 ml graduated cylinder wrapped with a heating tape set at about 50° C. About two thousand grams of glucose amide which is prepared from crystallized N-methyl glucamine in accordance with Example IV-B is eluted through the resin and is collected in about 200 g aliquots.

About 1800 g of eluate from the cationic column is then eluted through about 200 mls of regenerated Amberlite IR-410 strong anionic resin from Example VII. This column's temperature is also maintained at about 50° C. with the aid of an electric heat tape. The eluate is collected in sixteen, about 100 g aliquots.

Before resin treatment, analysis of the glucose amide indicates the following approximate quality and composition.

Transmittance at about 360 nm=74.1%
N-methyl glucamine=2.8%
Fatty Acid/Methyl Ester=4.9%
Glucose amide=55.6%
Ester Amide=0.2%

After resin treatment, both the color quality and composition of the product are greatly improved.

Transmittance at 360 nm=93.3%
N-methyl glucamine=0.1%
Fatty Acid/Methyl Ester=0.6%
Glucose amide=55.5%
Ester Amide=0.1%

EXAMPLE VII

A second method for regeneration of strong base anionic ion exchange resin after exhaustion by polyhydroxy amide elution is conducted as follows.

Ethanolic HCl solution is prepared by adding about 27.4 of concentrated (about 36.5 wgt %) HCl to about 972.6 g 3A ethanol.

A dilute solution of about 7 mole ethoxylated lauryl alcohol is prepared by dissolving about 9 g of ethoxylate in about 9 g of ethanol and about 1482 g of warm, distilled water.

About four hundred-fifty ml of exhausted resin, is packed in a 500 ml graduated dispensing cylinder, wrapped in a heating tape and held at about 50° C. The resin is washed with about one liter of warm distilled water to remove the residual amide. About one liter of warm, about 5% aqueous HCl is eluted through the resin to acidify. The column is allowed to set for about two hours at about 50° C. to allow the fatty acid to migrate to the surface of the resin. The column is back washed with about 1½ liters of warm ethoxylate solution to remove the fatty acid from the column.

The resin is then regenerated by slowing eluting about 1½ liters of about 5% aqueous NaOH solution through the resin. The resin is then washed with distilled water until the pH is about 8.

The cationic resin is regenerated in the same manner as described in Example VII.

When glucose amide prepared in the manner described in Example IV-A, having an amber color and measuring about 32.1% Transmittance at about 360 nm, is passed through these ion exchange resins, the color improves to a pale straw color measuring about 82.2% Transmittance at about 360 nm.

EXAMPLE VIII

N-methyl glucamine with good color stability and which subsequently produces good quality glucose amide is prepared in the following manner.

Approximately a two gallon autoclave is charged with about 360 g of Grace 4200 Raney nickel catalysts as a 50% suspension in water, about 920 g of 50% methyl amine and about 1000 g water. The reactor is pressurized to about 1500 psig with hydrogen. The reactor contents are heated to about 50° C. while stirring. To this is charged about 2600 g of CLEARSWEAT™ 99DE corn syrup and the contents are reacted at about 50° C. for about two hours. Fresh hydrogen is added to maintain the pressure as it is consumed by the reaction. A sample is removed from the reactor at the end of about two hours and its composition measured to be approximately:

N-methyl glucamine=95.0% n-glucosylamine=1.0% glucose=1.0% sorbitol=0.9%

This material was light yellow in color and upon subsequent reaction to glucose amide in accordance with the procedure described in Example IV-A results in a product that is very dark in color.

The reaction mixture remaining in the autoclave is now subjected to a temperature increase from about 50° C. to about 100° C. over the course of about 60 minutes while hydrogen pressure was maintained at about 1500 psig. After about 100° C. is reached, the reactor is quickly cooled under hydrogen pressure by introducing cooling water to the reactor coil. When the mixture has cooled to about 30°–50° C., the material is discharged from the reactor. Its composition is approximately:

N-methyl glucamine=97.3% n-glucosylamine non-detectable glucose non-detectable sorbitol=0.8%

This water white material is used to produce glucose amide in accordance with the procedure used in Example IV-A and results in a product that is pale yellow in color.

EXAMPLE IX

Amides Made from Crystallized NMG and Base Treated Ester

About 49.1 kg of Procter & Gamble CE-1295 methyl ester is charged to a 72 liter distillation flask equipped with a condenser and receiver. About 900 g of sodium methoxide solution (about 25% by weight in methanol) is added to the ester. At an absolute pressure of about less than 10 mm of Hg., the ester is heated to about 140° C. The distillate is condensed and collected in the receiver. The first about 618 g collected in the receiver is discarded; the remaining distillate is collected as a 'water white', low odor methyl laurate.

About 175.0 g of n-methyl glucamine crystals purified in accordance with Example III are dissolved in water to produce about 375.0 g of aqueous solution. This solution is charged to a standard one liter reaction flask set up comprising a mechanical stirring blade, condenser, and receiver. Over the course of about two hours and forty minutes, the solution is gradually heated to about 130° C. and the pressure is reduced to about 26 inches of Hg vacuum to remove the water which is condensed and collected in the receiver.

To the dehydrated n-methyl glucamine is added about 195.9 g of the distilled methyl laurate described above and about 36.5 g of propylene glycol. After stirring, about 14.5 g of sodium methoxide solution (about 25% by weight in methanol) is added to the reactor and the time is recorded. The mixture is allowed to cool to about 85° C. as methanol is distilled off under atmospheric pressure. After about 30 minutes no more methanol is visibly distilling so vacuum is slowly applied to the reaction vessel to strip out the remaining methanol and drive the reaction to completion. When the vacuum reaches about 25 inches of Hg without excessive foaming the reaction is complete. After breaking the vacuum with nitrogen, about 123.0 g water and about 72.3 g ethanol are added to the mixture. The resulting glucose amide solution is 'water white' in color and measures as 95% Transmission at 420 nm.

EXAMPLE X

Amides Prepared Using Triglycerides

Triglyceride reactants include CRISCO® oil, palm oil, sunflower oil, canola oil, rapeseed oil, coconut oil palm stearine, and the corresponding hydrogenated oils. The catalysts are alkali metal salts of monohydric alcohols, or polyhydroxy alcohols, e.g., sodium methoxide. The reaction medium is a nonionic surfactant, e.g., NEODOL® 10-8 or 23-3, or GENAPOL 26-L-5.

The reaction is conducted in a melt. The N-methylglucamine at a mole ratio of from about 2.3:1 to about 2.9:1 based upon the triglyceride, nonionic surfactant and triglyceride are co-melted at about 120°–140° C. under vacuum in about 30 minutes. About 7.5 mole %, based upon the N-methyl glucamine, of sodium methoxide is added to the reaction mixture. The reaction mixture becomes homogeneous in seconds. The reaction mixture is immediately cooled to about 85° C. The reaction mixture is maintained under vacuum for about 1–2 hours and is complete at this point.

In an alternate process, the N-methylglucamine is mixed at room temperature with the nonionic surfactant, triglyceride, and catalyst. The mixture is heated to 85°–90° C. under, alternatively, vacuum and nitrogen. The reaction mixtures become clear in one to one and a half hours. The reaction mixtures are maintained at about 85° C. for about 2–3 hours.

More specifically, about 127.45 g of N-methylglucamine powder is added to a 500 ml three-necked, round-bottom, flask equipped with an internal thermometer, vacuum line, nitrogen line, and mechanical stirrer. The N-methylglucamine is melted at about 130°–140° C. and dried under vacuum. Hardened palm kernel oil (about 156.41 g) is added to a separate 500 ml three-necked, round-bottom, flask equipped with an internal thermometer and a vacuum line. The hardened palm kernel oil is melted at about 130°–140° C. and dried under vacuum. The dried hardened palm kernel oil and about 31.54 g propylene glycol are added to the N-methylglucamine with mixing. About 1.76 g sodium methoxide as a 25% mixture with methanol is added to this mixture with mixing and the methanol is removed by vacuum. The mixture is homogeneous in about 1.5 minutes, at which time, cooling is applied. The mixture is cooled to about 90° C. in about seven minutes and maintained at this temperature for about 85 minutes. The mixture is poured out and the analysis was done by gas chromatography.

Removing the water from the reactants minimizes the formation of fatty acid. Preferably, the water level is less than about 0.1%.

EXAMPLE XI

Treatment of Amide with Borohydride

About two hundred grams of a glucose amide are added to a one liter, three-necked, reaction flask fitted with a thermometer on a top load balance. The reactor is transferred to a heated mantle and connected to a mechanical stirrer.

The temperature is raised to, and maintained at, about 38° C. throughout the treatment period. About 1.23 g of commercial sodium borohydride and about 0.20 g of powdered sodium borohydride are added to the reactor.

There is about 0.49 g of sodium hydroxide in the borohydride, which raises the pH from about 8.7 to about 10.4. The starting color of the amide is about 54% transmission at 420 nanometers and after about two hours of treatment the transmission is about 76%. The final pH of the solution is lowered to about 8 with 31% hydrochloric acid.

The pH of 10.4 results in increased production of soap, but a pH of more than about 10 is required for borohydride stability. Untreated N-methylglucamine amide typically has a soap content of about 3.09. The pH/soap content of borohydride treated N-methylglucamine amide varies approximately as follows: 10.1/3.14; 10.3/3.16; 10.6/3.17; and 11.0/3.41. As a result, the pH should be less than about 10.9 during treatment.

EXAMPLE XII

Polyhydroxy fatty acid amide surfactant solution as in Example II before purification, having a % transmission below about 70%, is treated with hydrogen in a high pressure stirred reactor, heated by an internal coil connected to a steam/water mixing apparatus. The surfactant solution contains, approximately: 60% surfactant, 22% water, 12% ethanol, and 6% propylene glycol. About 1000 g of the solution is slurried with about 1.2 g of palladium catalyst (5% palladium on carbon) wetted to about 50% moisture. The reactor is sealed and the agitator started at about 500 rpm. The reactor is repeatedly (five times) slowly pressurized to about 200 psi and then slowly vented. The reactor is then pressurized to about 400 psi and the agitator increased to about 1200 rpm. The temperature is raised to about 66° C. and the reaction carried out for about two hours and the product filtered under hydrogen pressure to remove catalyst. The % transmission is now more than about 80%.

What is claimed is:

1. In an amide-forming reaction for preparing amides of N-alkylamino polyols comprising reacting a source of fatty acyl groups such as fatty acids, fatty acid anhydrides, and fatty acid esters and an N-alkylamino polyol in an organic hydroxy solvent in the presence of a base catalyst, said reaction being carried out under non-oxidizing conditions, the step of selecting as reactants a source of fatty acyl groups selected from the group consisting of fatty acids, fatty acid anhydrides, fatty acid esters, and mixtures thereof having greater than 98% transmittance at 460 nm and an N-alkylamino polyol having a Gardner Color of less than 1.

2. The process of claim 1 in which the purity of the N-alkylamino polyol is improved by a process of crystallization of the N-alkylamino polyol from an aqueous solution or water/organic solvent mixture and recovering the N-alkylamino polyol.

3. The process according to claim 2 wherein crystallization is carried out by cooling an aqueous mixture of the N-alkylamino polyol to 0°–10° C., and isolating highly pure crystals of the N-alkylamino polyol from the supernatant solution by filtration and/or centrifugation.

4. The process according to claim 3 wherein an aqueous mixture of said N-alkylamino polyol is concentrated to at least about 70% solids prior to cooling, and then adding from about 10 to about 200 parts of an organic solvent to the concentrated solution.

5. The process according to claim 4 wherein the resulting filter cake, or centrifuge cake, is washed with from about 0.25 to about 1.25 parts of chilled, 0°–5° C. solvent.

6. The process according to claim 1 wherein said reaction is carried out in an organic hydroxy solvent in the presence of a base catalyst at a temperature of from about 40° C. to about 135° C. for a period of time that is less than about three hours.

7. The process according to claim 6 wherein said reaction is carried out at a temperature of from about 50° C. to about 80° C.

8. The process according to claim 6 wherein said reaction is carried out at a temperature of from about 50° C. to about 80° C. for a period of time that is less than about two hours.

9. The process according to claim 8 wherein the resulting N-alkyl polyhydroxy amine amide is treated with ion exchange resin.

10. The process according to claim 9 wherein said ion exchange resin is a mixture of acid and base resins.

11. The process according to claim 10 wherein said N-alkyl polyhydroxy amine amide is treated first with acid ion exchange resin to convert any soap that is present to fatty acid and remove any residual amine that may be present and then is treated with base ion exchange resin to remove the fatty acid.

12. The process according to claim 8 wherein said N-alkyl polyhydroxy amine amide is treated with reducing bleach.

13. The process according to claim 12 wherein the N-alkyl polyhydroxy amine is N-methylglucamine.

14. The process according to claim 13 wherein said source of fatty acyl groups is fatty acid ester.

15. The process according to claim 14 wherein the catalyst is used at a level of from about 5 to about 8 mole % of the fatty acid ester.

16. The process according to claim 6 wherein the organic solvent is selected from the group consisting of: methanol, ethanol, propanol, iso-propanol, butanol, glycerol, 1,2-propylene glycol, 1,3-propylene glycol, and mixtures thereof.

17. The process according to claim 6 wherein the pressure is held at a vacuum of less than about 200 mmHg and the solvent is removed from the reaction product in less than about one hour.

18. The process according to claim 17 wherein said amount of time is less than about one-half hour.

19. A process, carried out under non-oxidizing conditions, for preparing amides of N-alkylamino polyols comprising (1) reacting a source of fatty acyl groups selected from the group consisting of fatty acids, fatty acid anhydrides, fatty acid esters, and mixtures thereof having greater than 98% transmittance at 460 nm with an N-alkylamino polyol having a Gardner Color of less than 1; (2) removing from an aqueous solution of said amides of N-alkylamino polyols an impurity selected from the group consisting of amine, fatty acid, and mixtures thereof by a step comprising treating said solution with ion exchange resin and then, when said ion exchange resin is a strong base ion exchange resin containing fatty acyl anion groups, regenerating said strong base ion exchange resin by a process comprising acidifying the resin to form fatty acids corresponding to the fatty acyl anion groups and removing the fatty acids by dissolving them in organic solvent; and (3) removing color body, color body precursor, or mixtures thereof from said amides of N-alkylamino polyols comprising the step of treating said amides of N-alkylamino polyols with reducing bleach.

* * * * *